(12) United States Patent
Kollmeier et al.

(10) Patent No.: US 6,295,467 B1
(45) Date of Patent: Sep. 25, 2001

(54) METHOD AND DEVICE FOR DETECTING A REFLEX OF THE HUMAN STAPEDIUS MUSCLE

(76) Inventors: Birger Kollmeier, Hörneweg 50a, Oldenburg (DE), D-26129; Joachim Neumann, Friedensplatz 2, Oldenburg (DE), D-26122

( * ) Notice: Subject to any disclaimer, the term of this patent is extended or adjusted under 35 U.S.C. 154(b) by 0 days.

(21) Appl. No.: 09/214,989
(22) PCT Filed: Jul. 10, 1997
(86) PCT No.: PCT/DE97/01450
§ 371 Date: Jan. 15, 1999
§ 102(e) Date: Jan. 15, 1999
(87) PCT Pub. No.: WO98/03114
PCT Pub. Date: Jan. 29, 1998

(30) Foreign Application Priority Data
Jul. 18, 1996 (DE) .............................. 196 28 978

(51) Int. Cl.[7] .................................................. A61B 5/05
(52) U.S. Cl. ........................ 600/547; 600/559; 73/585; 73/587; 73/589; 179/1
(58) Field of Search ................................. 600/547, 546, 600/437, 559; 73/585, 589, 587; 179/1

(56) References Cited

U.S. PATENT DOCUMENTS

| 3,949,735 | * | 4/1976 | Klar et al. | 600/559 |
| 4,009,707 | * | 3/1977 | Ward | 600/559 |
| 4,079,198 | * | 3/1978 | Bennett | 600/559 |
| 4,201,225 | * | 5/1980 | Bethea, III et al. | 600/559 |
| 4,289,143 | * | 9/1981 | Canavesio et al. | 600/559 |

FOREIGN PATENT DOCUMENTS 0674874A    10/1995    (EP) .

* cited by examiner

Primary Examiner—Marvin M. Lateef
(74) Attorney, Agent, or Firm—Collard & Roe, PC.

(57) ABSTRACT

The invention concerns a method of detecting a reflex of the human stapedius muscle, in particular for a hearing test. According to the method, the reflex is triggered by means of an acoustic signal, and the impedance or the variation in impedance brought about by means of the reflex at the eardrum is measured by means of a further acoustic signal. The object of the invention is to further improve the stapedius reflex audiometry method so that it can be applied in practice. To that end, at least two chronologically successive or mutually overlapping substantially identical acoustic signals are used. The information concerning a possible impedance variation at the eardrums obtained by forming the difference between the acoustic characteristics produced and registered by the signals.

8 Claims, 4 Drawing Sheets

METHOD AND DEVICE FOR DETECTING A REFLEX OF THE HUMAN STAPEDIUS MUSCLE

BACKGROUND OF THE INVENTION

1. Field of the Invention

The invention relates to a method for detecting a reflex of the human stapedius muscle in particular for a hearing test, by which the reflex is triggered by means of an acoustic test signal having a frequency of, for example 500 Hz or higher, and with a sound level of at least 65 dB HL; and the impedance prior to and the impedance after the reflex on the tympanic membrane is measured by means of at least one acoustic measuring signal with a frequency of, for example about 220 Hz and with a sound level of clearly below 65 dB HL, said measuring signal lasting longer, if need be, and being compared by forming a difference between the corresponding measuring signals or measuring signal ranges.

Furthermore, the invention relates to a device for detecting a reflex of the human stapedius muscle, with a signal transmitter for emitting acoustic signals or sounds, and with a signal receiver, preferably a microphone for carrying out said method.

2. The Prior Art

In stapedius reflex audiometry of the type concerned herein, a reflex or the human stapedius muscle is used, which can be triggered by an acoustic stimulus, whereby sound stimuli exceeding a level of 80 or 90 dB HL (hearing level) are conventionally offered.

The level threshold above which the reflex of the stapedius muscle can be observed is referred to as the acoustic reflex threshold.

The stapedius muscle is the smallest muscle in the human body. It is located in the middle car and connected with the stapes, one of the auditory ossicles. Tensioning of said muscle changes the mechanical properties of the chain of auditory ossicles and thereby also the acoustic impedance on the tympanic membrane. It can be said in a simplified way that the sound reflection properties of the tympanic membrane change depending on the tensioning of the stapedius muscle, which changes not only the intensity and thus also the amplitude of a reflected sound, but also its phase as compared to the phase of the reflected signal when the stapedius muscle is relaxed.

Said described behavior of the stapedius muscle and the impedance variation resulting therefrom are used in stapedius reflex audiometry for the measurement, for example within the framework of a hearing test or other scientific function tests of a human ear.

The following procedure is conventionally employed in this connection: A continuous measuring sound with a frequency of, for example 226 Hz is emitted, such sound having a relatively lower level not sufficient for triggering the muscle reflex, and a short signal is additionally generated and emitted during the duration of the measuring sound in order to trigger the stapedius reflex. Said signal frequently has a sound level far above 80 dB HL and another frequency, for example the audiogram frequencies 500 Hz, 1 KHz, 2 KHz, and 4 KHz. The test signal also may be wide-banded (e.g. noise) and it may be repeated at short intervals.

As soon as the stapedius reflex has been triggered by the signal, the sound curve received by a signal receiver, for example by a microphone—with the auditory canal closed in most cases—changes due to the changed impedance on the tympanic membrane. Measured is in this connection the change in amplitude of the measuring sound reflected on the tympanic membrane.

Said measuring method exhibits little sensitivity because of the very minor variations of the reflected measuring sound, so that a stapedius reflex is not always safely detectable.

However, a method as described above is known from U.S. Pat. No. 3,949,735, by which the differences between the level of the reaction to the measuring sound prior to and after the reflex are more exactly detected by difference formation. However, a rectifier is employed for this purpose, which makes any later effect of phase information impossible.

Furthermore, the level employed for the test sound in the state of the art frequently reaches the range of the discomfort threshold, which is graded by test persons as unpleasant or insufferable. Therefore, the conventional stapedius reflex audiometry method cannot be applied unlimited with some test persons, in particular not with patients who shortly before suffered a sudden drop in hearing ability.

SUMMARY OF THE INVENTION

The invention has the object of rendering the stapedius reflex audiometry method more precise and less stressing for the test person in practical application.

According to the invention this object is achieved in that with omission of any usual measuring signal, use is made of at least two chronologically successive or mutually overlapping acoustic test signals, the latter being as identical as possible with respect to their frequencies and sound levels; and that the information about any possible variation in impedance on the tympanic membrane is obtained by means of forming the difference between the sound curves produced and registered by the test signals.

Other than with the conventional method, no distinction is made between the measuring signal and the test signal. Use is made instead only of test signals which are as identical as possible and presented in a rapid sequence. This may be two short sound pulses of identical frequency, or also two identical segments in a periodic signal (for example a sound or sound complex or a wide-banded noise).

The time sequence of the signals employed exploits the fact that the stapedius reflex requires a certain reaction time for reacting to the first test signal. Therefore, the time space between the test signals is coordinated in such a way that the second test signal is emitted at just the point in time when it can be assumed that the stapedius muscle had adequate reaction time for reacting to the first test signal provided it is capable of such a reaction at all because of the conditions present in the respective ear or the sound level employed.

The signal components recorded by the signal receiver, for example a microphone, are stored in a first analytical step, for example with a digital recording device, and subtracted from each other. Coupling between the sound-emitting device and the sound-recording device must be assured in this connection. The difference of the recorded test signals contains only one noise component in a system equally reacting to the first and the second test signals. When the system is changed, for example by a stapedius reflex that has been triggered by the first test signal, the difference signal is greater than the aforementioned noise.

The advantage with said method as defined by the invention consists, for example in that a distinctly lower level can be employed as compared to conventional stapedius reflex audiometry. This means that a more distinct distance from the discomfort threshold is maintained with the level employed, so that the method as defined by the invention is more pleasant for the test persons and that the number of test persons who can be used is increased as well.

The method as defined by the invention in particular offers the advantage that it is not only possible in this way to register a possible change in amplitude as with the conventional method, but also a shift in phase that is caused by the change in tension of the tympanic membrane as well. Such phase shift effects under certain circumstances a much greater difference signal and thus one that can be registered in a superior way.

Preferably, the time space between the test signals is selected in the order of magnitude of about 100 ms, whereby it is possible also, if need be, to employ several test signals that are chronologically staggered one after the other for detecting the curve of the reflex. Two successive separate, independent measurements should be spaced from each other in terms of time to such an extent that a certain recovery phase is available for the stapedius reflex. The time space should subsequently amount to about at least half a second. On the other hand, it is entirely desirable to carry out several measurements as defined by the invention in order to obtain a more precise measuring result in particular in view of statistical errors (averaging of the difference signals).

A device as defined by the invention for detecting a reflex of the human stapedius muscle for carrying out the afore-described method as defined by the invention is characterized by a timer for emitting two acoustic test signals following each other at a predeterminable time interval by means of the signal transmitter, and by a subtracter for forming the difference between the sound curve received by the signal receiver through the chronologically first test signal, and the sound curve obtained through the second test signal. The respective advantages have already boon described in connection with the method as defined by the invention.

Such time control, which assures that two test signals that are as identical as possible are emitted with a defined time space can be realized in a simple way, for example electronically.

A special advantage of the method as defined by the invention, and also of the device as defined by the invention lies in the fact that a device for recording otoacoustic emissions is substantially employed for the method as defined by the invention and thus as the device as defined by the invention, whereby it is entirely customary in connection with such emissions to emit different acoustic signals with defined time spacing relative to each other. However, such otoacoustic devices are not obviously suitable for stapedius reflex audiometry because of the entirely different measuring method and goal. Furthermore, the signals used for otoacoustic measurements have a lower stimulation level. Therefore, if an otoacoustic measuring device is employed for the method as defined by the invention, such a device would have to be designed and changed in view of the emission of test signals with higher levels. However, due to the fact that it is possible to employ existing apparatuses, conversion of the method as defined by the invention into commercial application is nonetheless quickly feasible.

It has to be mentioned supplmentarily that the method as defined by the invention can be carried out at least as quickly as conventional stapedius reflex audiometry, so that the duration of the session required for a test person needs not to be prolonged.

BRIEF DESCRIPTION OF THE DRAWINGS

Graphical explanations of the method as defined by the invention revealing also further inventive features are shown in the drawing, in which

FIG. 3 shows the result of a conventional stapedius reflex measurement after a signal input according to FIG. 2a.

DETAILED DESCRIPTION OF PREFERRED EMBODIMENTS

Figure 1:
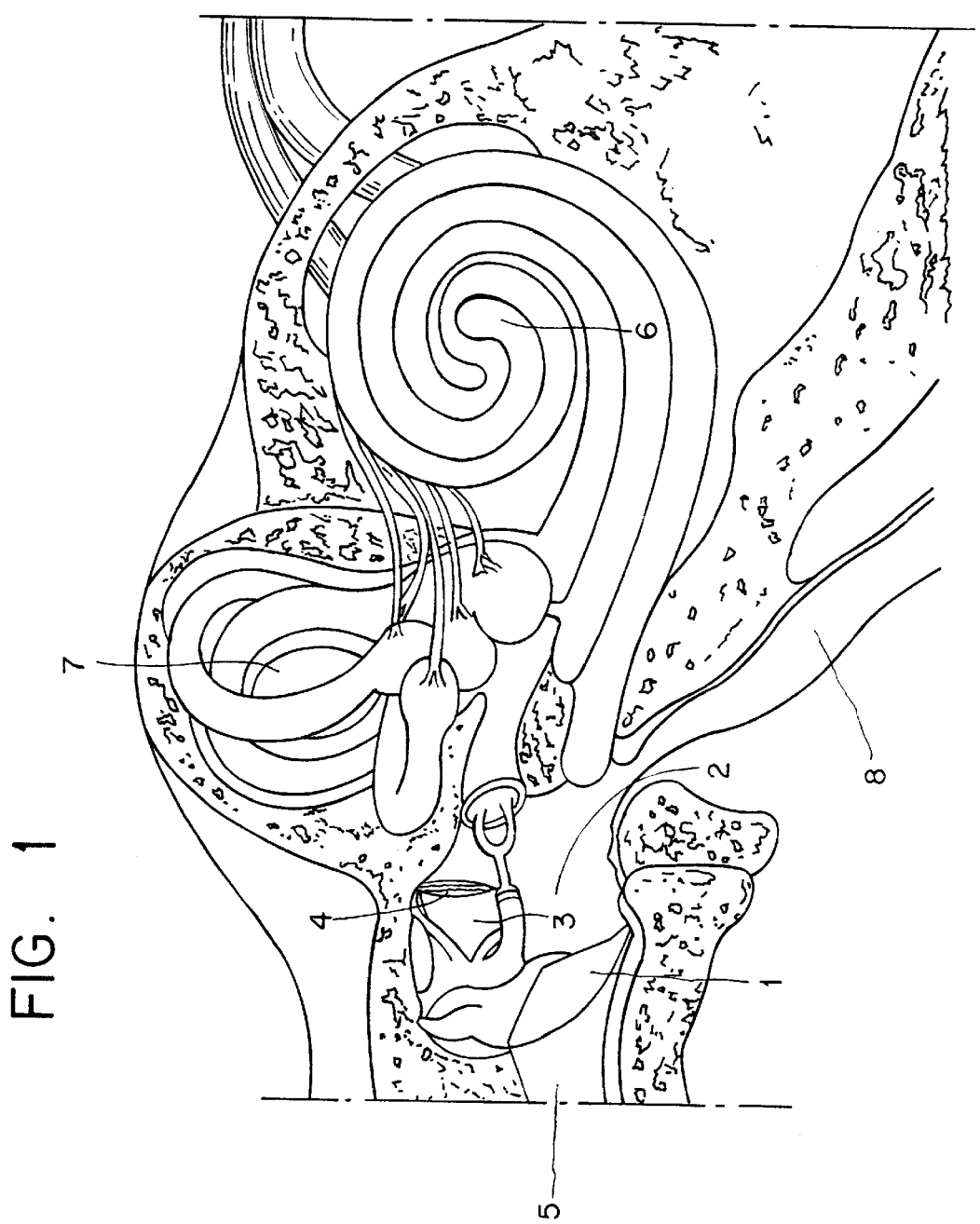
FIG. 1 shows the middle and internal ear regions of a human ear.

FIG. 1 shows the middle and internal ear regions of a human ear.

The drawing shows in particular the tympanic membrane 1, the tympanic cavity 2 with the auditory ossicles 3 located in said cavity and coupled to the tympanic membrane 1, and the stapedius muscle 4 attached to the stapes, one of the auditory ossicles.

Furthermore, it shows the external acoustic meatus 5, cochlea 6, the labyrinth 7, and the eustachian tube 8.

The tension and thereby also the impedance on the tympanic membrane 1 are changed with the help of the stapedius muscle.

In stapedius reflex audiometry, an acoustic signal transmitter and an acoustic signal receiver combined, for example in a rubber-like olive, are inserted in most cases in auditory meatus 5 in order to register or measure acoustic signals acting on tympanic membrane 5 and the impedance of tympanic membrane 1 through registration of the sound curve resulting due to such signals in auditory meatus 5.

Figure 2:
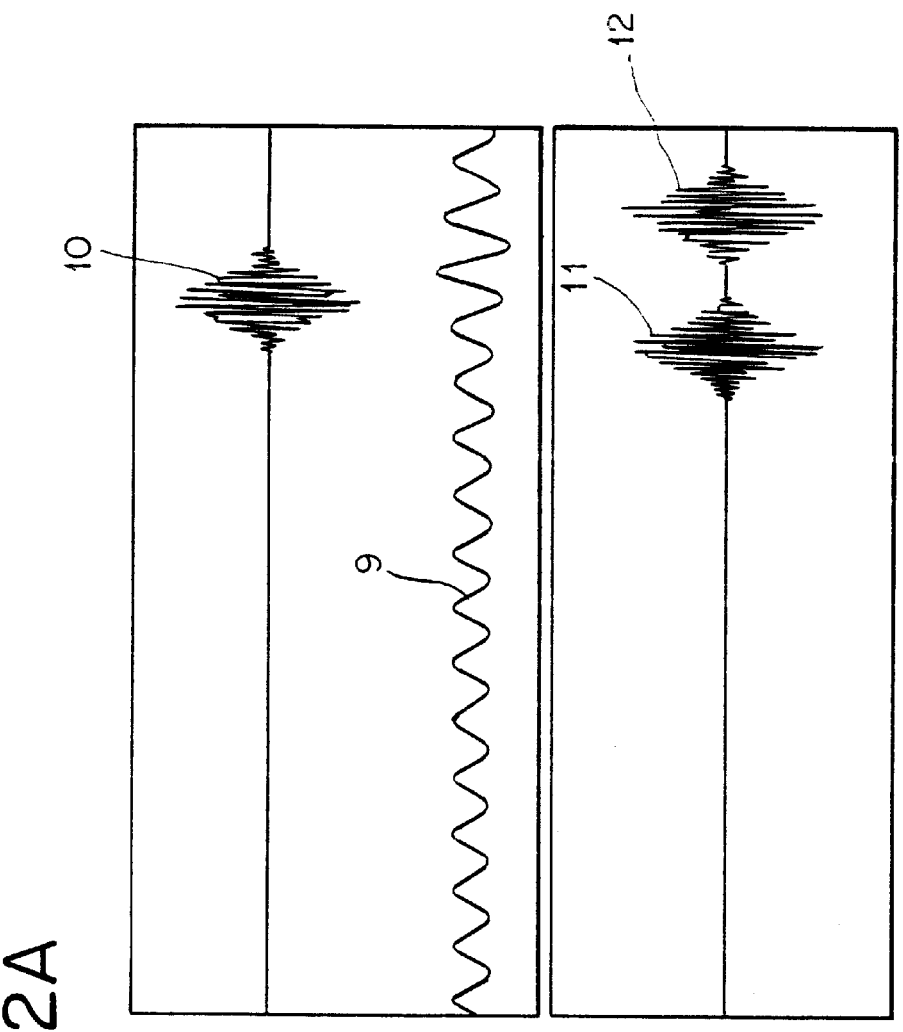
FIG. 2 shows the signal admission in conventional stapedius reflex audiometry as well as also by comparison with the method as defined by the invention.

FIG. 2 shows within the framework of FIG. 2a the signal admission in a conventional stapedius reflex audiometry, and in the region of FIG. 2b the signal admission by the method as defined by the invention.

In connection with the conventional method according to FIG. 2a, a continuous measuring sound 9 is employed, whose possible change in its sound curve is measured after a possible stapedius reflex. With the conventional method, the stapedius reflex is triggered by a separate short-time test sound 10. It can be seen also in drawing 2a, where time units are plotted on the abscissa, the measuring sound 9 and the test sound 10 differ from each other with respect to their frequencies and also in regard to their amplitudes, which are plotted untrue to scale on the ordinate. Test sound 10 has a significantly higher frequency and a much higher level, for example in the 90 dB HL range plus/minus about 10 dB.

With the signal curve shown by way of example for the method as defined by the invention in FIG. 2b, two chronologically successive signals are used, namely a first sound pulse 11 and a second sound pulse 12 shortly following the former, the latter having been generated identically.

Surprisingly, both sound pulses 11, 12 may have a clearly lower sound level than the test sound 10 in the conventional method, for example a level that is lower by about 8 dB.

Sound pulse 11, which is the first in time in the method as defined by the invention, triggers the stapedius reflex, which requires a certain reaction time. The time space of the second sound pulse 12 relative to the first sound pulse 11 is coordinated with said reaction time in the method as defined by the invention. Sound pulse 12 is emitted when, upon expiration of a sufficient reaction time, a stapedius reflex already has to be expected at just that time. The time space between the two sound pulses 11 and 12 is in about the order of magnitude of 100 ms.

Other than shown in FIG. 2b it is not absolutely required to use as signals the sound pulses 11, 12, and it is not absolutely necessary to emit separate acoustic wave trains. It is rather possible to emit any signals which, however, must have been identically generated in at least two chronologically successive or overlapping time segments.

Said segments can be defined or "cut out" from a continuous wave train with suitable electronic means with respect to their time spacing and their time expanse.

Figure 3:
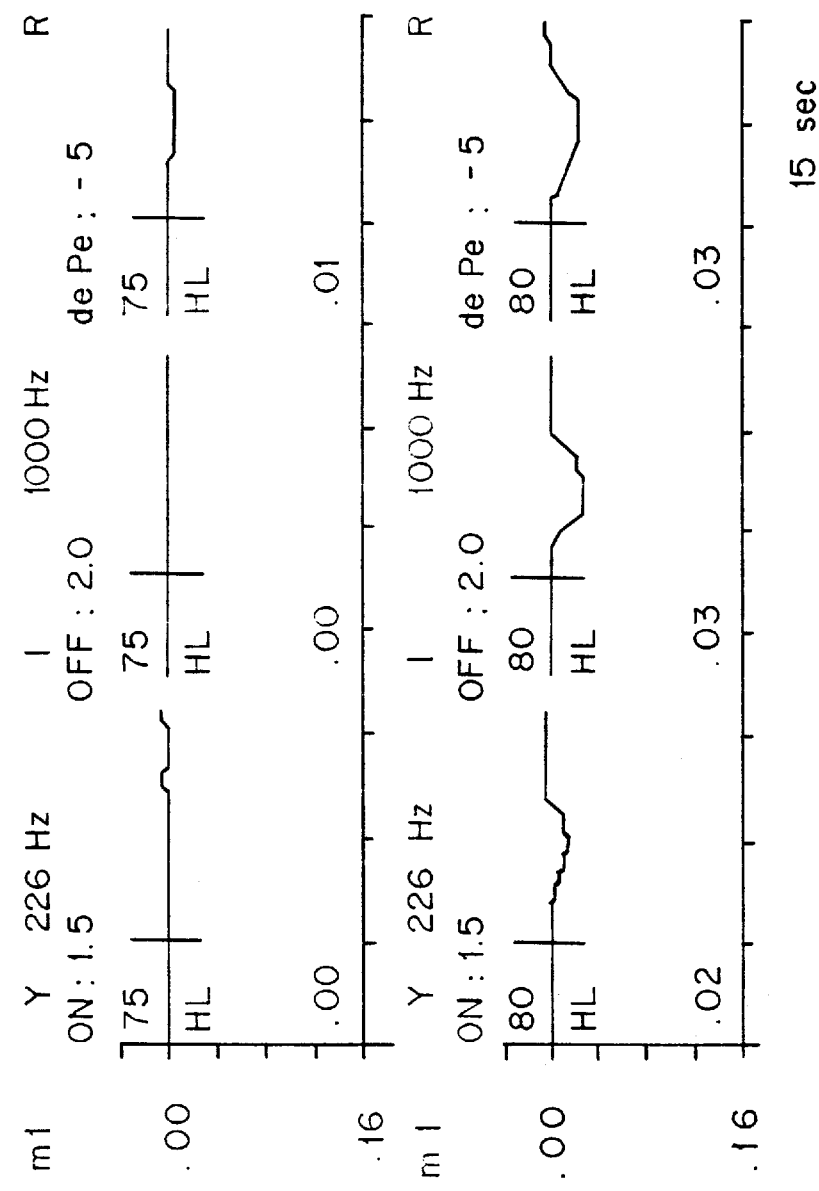

FIG. 3 shows by way of example a measuring result based on a conventional measurement with an input signal curve as in FIG. 2a. Said FIG. 3 in particular shows that the variation of continuous measuring sound 9 resulting from a stapedius reflex stimulated by test sound 10—which variation has to be registered and measured for the measurement—can be detected and measured only with extreme difficulty because it is possible only to take into account amplitude changes which, percentage-wise, are small as compared to the original amplitude, so that the corresponding measuring errors are included to a high degree in the measurements.

Figure 4:
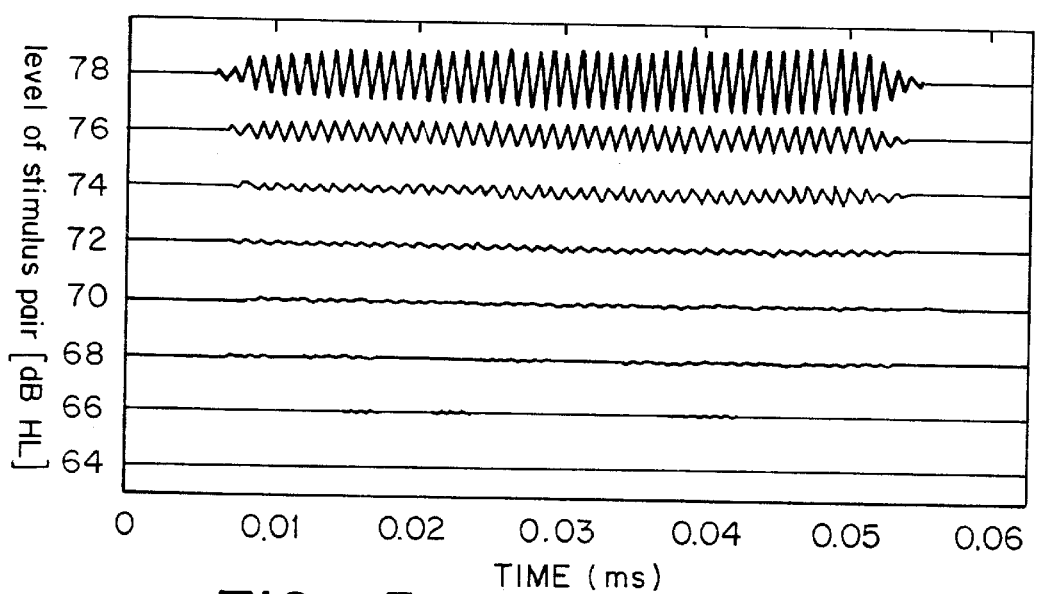
FIG. 4 shows a measuring result according to the method as defined by the invention after a signal input according to FIG. 2b.

In comparison to the above, FIG. 4 shows by way of example a measuring result of a method as defined by the invention, where a signal curve according to FIG. 2b has been used as the input signal curve.

What is measured in the method as defined by the invention is the difference of signal 11 relative to the signal 12 that was changed by the stapedius reflex previously triggered by the signal 11, or of the sound curves obtained in the external auditory meatus 5 because of signals 11, 12 both prior to and after the stapedius reflex, whereby it has to be taken into account that the two signals 11, 12 are identical at the time of their emission.

As shown in FIG. 4, the difference to be measured differs significantly from zero with a functioning stapedius reflex even though the input signals were identical, as mentioned before, because the impedance on the tympanic membrane has changed due to the reflex.

The level of signals 11, 12 is plotted in dB HL (hearing level) in FIG. 4 on the ordinate. The time curve of the difference signal is plotted in milliseconds on the abscissa.

Therefore, FIG. 4 shows that the difference of the two received signals is clearer at higher levels simply because the reflex is triggered more strongly at a higher level. However, a difference signal is distinctly recognizable even at very low levels as compared to those employed in connection with the conventional method.

Figure 5:
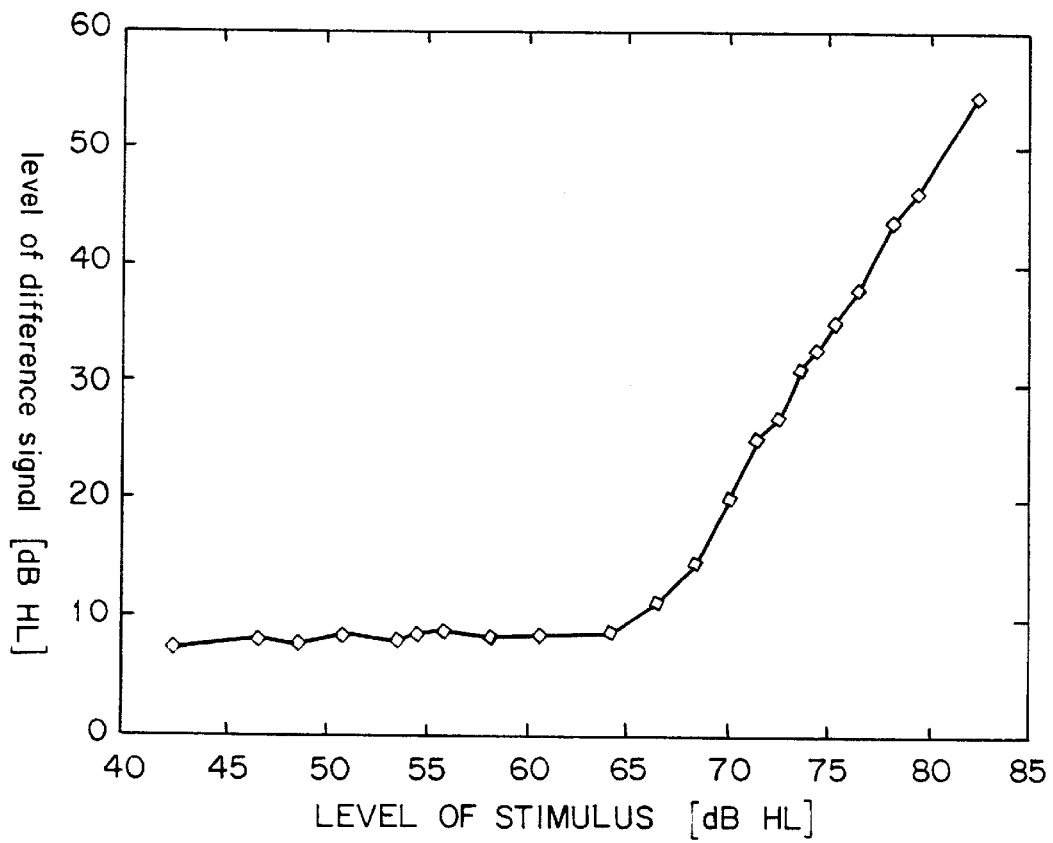
FIG. 5 shows the signal differences obtained as the result of measurements according to the invention, as a function of the stimulation level.

The relation between the level employed and the intensity of the difference signal with respect to FIG. 4 is plotted again in FIG. 5.

It can be seen in FIG. 5 that with the signals 11, 12 used with a frequency of 1 kHz, the reflex threshold is at about 65 dB HL. The desired stapedius reflex therefore occurs only at a higher signal level. If a higher level is employed accordingly, however, a clear difference signal results immediately provided the reflex is actually triggered in a healthy ear.

It is particularly shown in FIG. 5 that a clear difference signal can be observed in a range of about 75 dB HL when the method as defined by the invention is used, whereas conclusive measurements on the same test person according to the representation in FIG. 3 can be obtained with the conventional method only at a level of approximately 85 dB HL.

Therefore, it can be noted in summary that when the method as defined by the invention is employed, the contraction of the stapedius muscle can be observed with a distinctly lower signal level as compared to a conventional method. Therefore, the level employed can be more distinctly below the "discomfort threshold". This permits in particular the application of the method as defined by the invention in connection with test persons who, due to a sudden drop in hearing ability, may not be measured at higher levels.

The duration of execution of a measurement according to the method as defined by the invention approximately corresponds with the duration of a measurement by a conventional method. However, due to more significant measuring results with the method as defined by the invention, the number of measurements that have to be averaged in order to minimize the statistical error could be reduced, so that this would finally result in a shorter overall duration of the measurement.

What is claimed is:

1. A method of detecting a reflex of the human stapedius muscle for a hearing test, in which the reflex is triggered by means of an acoustic test signal of a relatively higher frequency range and with a sound level of at least 65 dB HL; the impedance prior to the reflex and the impedance after the reflex on the tympanic membrane are measured by means of at least one, if necessary longer-lasting measuring signal of a relatively lower frequency range and with a sound level of clearly below 65 dB HL; and compared by forming the difference between the respective measuring signals or measuring signal ranges, comprising with omission of any usual measuring signal, using at least two chronologically successive or mutually chronologically overlapping test signals, said overlapping test signals being as identical as possible with respect to their frequency parameters and their sound level; and obtaining information of any possible impedance variation on the tympanic membrane by means of forming the difference between the sound curves produced and registered by said test signals.

2. The method according to claim 1, comprising employing as test signals two segments of a longer-lasting signal, said segments being defined with respect to their time duration.

3. The method according to claim 1, comprising selecting the time space between a chronologically first test signal and a successive second test signal approximately corresponding with the time for triggering the stapedius reflex.

4. The method according to claim 1, comprising selecting the time space between separate, independent measurements to be about 0.5 second or longer.

5. The method according to claim 1, comprising using the measurement of the phase information of the resulting sound curves.

6. The method according to claim 1, comprising using sounds having different frequencies or wide-banded signals.

7. A device for detecting a reflex of the human stapedius muscle comprising a signal transmitter for emitting acoustic test signals, a signal receiver, a timer for emitting two acoustic test signals by means of the signal transmitter, said test signals being successively emitted with a predetermined time space; and a subtracter for forming the difference between the sound curve received by the signal receiver and obtained through the chronologically first test signal, and the sound curve obtained through the chronologically second test signal.

8. The device according to claim 7, comprising a device suitable for otoacoustic measurements, but devised with respect to its signal transmitter for emitting test signals having higher sound levels as compared to signals required in otoacoustic measurements.

* * * * *